United States Patent
Forstein (10) Patent No.: US 11,259,872 B2
(45) Date of Patent: Mar. 1, 2022

(54) INTRAOPERATIVE ADJUSTMENT OF A PRE-OPERATIVELY PLANNED IMPLANT CAVITY TO IMPROVE IMPLANT FIT

(71) Applicant: Think Surgical Inc., Fremont, CA (US)

(72) Inventor: Micah Forstein, Fremont, CA (US)

(73) Assignee: Think Surgical Inc., Fremont, CA (US)

( * ) Notice: Subject to any disclaimer, the term of this patent is extended or adjusted under 35 U.S.C. 154(b) by 341 days.

(21) Appl. No.: 16/521,672

(22) Filed: Jul. 25, 2019

(65) Prior Publication Data
US 2020/0030036 A1    Jan. 30, 2020

Related U.S. Application Data

(60) Provisional application No. 62/703,038, filed on Jul. 25, 2018.

(51) Int. Cl.
| | |
|---|---|
| *A61B 34/10* | (2016.01) |
| *A61B 17/17* | (2006.01) |
| *A61B 34/30* | (2016.01) |
| *A61B 90/00* | (2016.01) |
| *A61B 17/00* | (2006.01) |

(52) U.S. Cl.
CPC ............ *A61B 34/10* (2016.02); *A61B 17/17* (2013.01); *A61B 34/30* (2016.02); *A61B 90/06* (2016.02); *A61B 2017/00057* (2013.01); *A61B 2017/00092* (2013.01); *A61B 2034/104* (2016.02); *A61B 2034/105* (2016.02); *A61B 2034/107* (2016.02); *A61B 2090/065* (2016.02)

(58) Field of Classification Search
CPC ..................................... A61B 34/10–2034/108
See application file for complete search history.

(56) References Cited

U.S. PATENT DOCUMENTS

| | | | | |
|---|---|---|---|---|
| 5,418,711 A | * | 5/1995 | Pomerleau | B26D 5/00 700/134 |
| 2005/0054917 A1 | * | 3/2005 | Kitson | G16H 30/40 600/427 |

* cited by examiner

*Primary Examiner* — Zade Coley
(74) *Attorney, Agent, or Firm* — Blue Filament Law PLLC (57) ABSTRACT

A method and system are provided to intraoperatively adjust the dimensions of a pre-operatively planned implant cavity to improve implant fit in a bone. The method includes obtaining a preoperative image data set of the bone. A surgical plan is generated using the image data set and/or a three-dimensional (3-D) bone model of the patient's bone generated from the image data set. Intraoperatively, the patient's bone is exposed and registered to the surgical plan and a computer assisted surgical system. The computer assisted surgical system having a cutting tip and a force sensor for sensing actual forces exerted on the cutting tip as an initial cut is created on the bone at a first bone region. Based on the difference between the actual cutting force and the expected cutting force in the plan, the dimensions of the cavity are adjusted accordingly.

19 Claims, 5 Drawing Sheets

INTRAOPERATIVE ADJUSTMENT OF A PRE-OPERATIVELY PLANNED IMPLANT CAVITY TO IMPROVE IMPLANT FIT

RELATED APPLICATIONS

This application claims priority benefit of U.S. Provisional Application Ser. No. 62/703,038 filed 25 Jul. 2018, the contents of which are hereby incorporated by reference.

TECHNICAL FIELD

The present invention generally relates to the field of computer-assisted orthopedic surgery, and more particularly to a system and method to intraoperatively adjust the dimensions of a pre-operatively planned implant cavity to improve implant fit in a bone.

BACKGROUND

Throughout a lifetime, bones and joints become damaged and worn through normal use, disease, and traumatic events. Arthritis is a leading cause of joint damage, which can cause cartilage degradation, pain, swelling, stiffness, and bone loss overtime. If the pain associated with the dysfunctional joint is not alleviated by less-invasive therapies, the joint may need to be replaced with a procedure called total joint arthroplasty (TJR). TJR is an orthopedic surgical procedure in which the typically worn articular surfaces of the joint are replaced with prosthetic components, or implants. TJR typically requires the removal of the articular cartilage of the joint including a varying amount of bone. This cartilage and bone is then replaced with synthetic implants, typically metal and plastic, which form the new synthetic joint surfaces.

The accurate placement and alignment of the implants on the bone is a large factor in determining the success of a TJR procedure. A slight misalignment of an implant may result in poor wear characteristics, reduced functionality, poor clinical outcomes, and decreased longevity. Therefore, several TJR procedures are now performed with computer-assistance, and even more advanced procedures utilize robotic surgical systems. One such robotic surgical system is the TSOLUTION ONE® Surgical System (THINK Surgical, Inc., Fremont, Calif.), which aids in the planning and execution of total hip arthroplasty (THA) and total knee arthroplasty (TKA). The TSOLUTION ONE® Surgical System includes: a pre-operative planning software program to generate a surgical plan using an image data set and/or 3-D models of the patient's bone, computer-aided design (CAD) models of several implants; and an autonomous surgical robot that precisely mills the bone to receive an implant according to the surgical plan.

Figure 1:
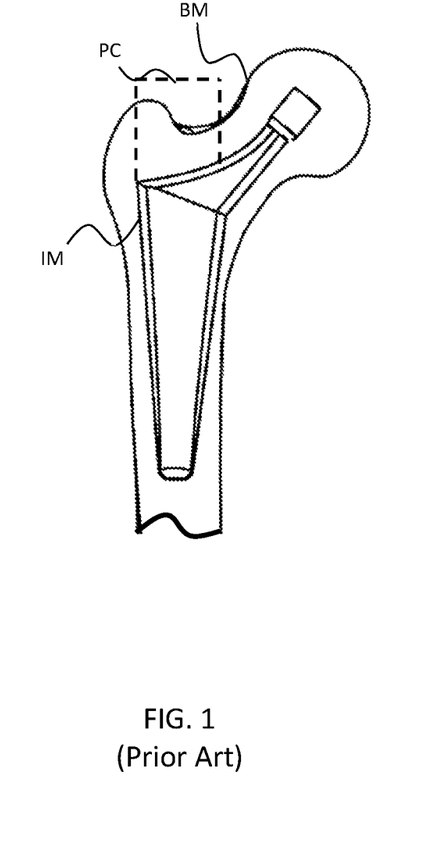
FIG. 1 is a prior art view of a bone model BM having an implant model IM positioned therein.

With regard to pre-operative planning, prior art FIG. 1 depicts a bone model BM having an implant model IM positioned therein. The user may adjust the model, size, position and orientation (POSE) of the implant model IM to designate the best fit, fill, and position for the implant. The model, size, and POSE of the implant model IM in the bone model BM also designates the POSE and dimensions for an implant cavity to be made in the bone to receive the implant. The dimensions of the implant cavity may substantially resemble the dimensions of the implant and also includes regions to be cut (e.g., the dotted region above the implant referred as the pre-cut PC) to gain access to create the implant shape in the planned POSE. The dimensions of the implant cavity may be undersized relative to the implant shape to create a press-fit interaction between the implant and the bone. The dimensions of the implant cavity may further lack certain portions of the implant shape (e.g., the distal tip region) depending on several factors such as the ability of a milling tip to reach and mill those portions of the bone. In any case, the surgical plan is saved and transferred to the surgical robot, where the surgical robot executes a cut-file to create the implant cavity according to the plan.

One problem, however, is the lack of bone quality data to aid in planning the procedure. It is difficult to ascertain the actual quality of the patient's bone from a simple computed tomography (CT) scan. It is contemplated that a user may adjust one or more parameters of the plan if the user has additional bone quality data. For example, if the user knows the patient has poor bone quality, the user may reduce the size of the implant cavity to increase the press-fit and retain as much bone as possible. The user may further adjust the implant cavity at specific bone regions to improve the fit. Overall, this may improve the longevity of the implant, reduce stress-shielding effects, improve initial implant stability, improve osseointegration, and reduce the occurrence of subsidence and revision. But once again, obtaining accurate bone quality data pre-operatively is difficult and may require additional radiation.

Thus, there exists a need for a system and method to intraoperatively adjust the dimensions of a pre-operatively planned implant cavity to improve implant fit in a bone.

SUMMARY OF THE INVENTION

A method is provided to intraoperatively adjust the dimensions of a pre-operatively planned implant cavity to improve implant fit. The method includes obtaining an image data set of a bone and generating a surgical plan using the image data set. The surgical plan includes: i.) one or more expected cutting forces or cutting temperatures for one or more bone regions; and ii.) a location for the pre-operatively planned implant cavity to receive an implant in a predetermined position and orientation (POSE). The method further includes transferring the surgical plan to a computer assisted surgical system, registering the bone to the surgical plan and to the computer assisted surgical system, and measuring an actual cutting force or cutting temperature on a cutting instrument while cutting a first bone region. The actual cutting force or cutting temperature is compared to the one or more expected cutting forces or cutting temperatures, and a dimension of the cavity is adjusted based on the comparing to improve implant fit.

A computer assisted surgical system is provided that includes a surgical robot, a computing system, and at least one of a mechanical arm or a non-mechanical tracking system. The computing system includes one or more processors for performing the method to intraoperatively adjust the dimensions of a pre-operatively planned implant cavity to improve implant fit.

BRIEF DESCRIPTION OF THE DRAWINGS

The present invention is further detailed with respect to the following drawings that are intended to show certain aspects of the present of invention, but should not be construed as limit on the practice of the invention, wherein.

DETAILED DESCRIPTION

The present invention has utility as a system and method to intraoperatively adjust the dimensions of a pre-operatively planned implant cavity to improve implant fit in a bone. The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment may be deleted from the embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations, and variations thereof.

Further, it should be appreciated that although the systems and methods described herein make reference to the proximal femur, the systems and methods may be applied to other bones and joints in the body illustratively including the knee, ankle, elbow, wrist, skull, and spine, as well as revision of initial repair or replacement of any of the aforementioned bones or joints.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

As used herein, the term "pre-operative bone data" refers to bone data used to pre-operatively plan a procedure before making modifications to the actual bone. The pre-operative bone data may include one or more of the following. An image data set of a bone (e.g., computed tomography, magnetic resonance imaging, ultrasound, x-ray, laser scan), a virtual generic bone model, a physical bone model, a virtual patient-specific bone model generated from an image data set of a bone, or a set of data collected directly on a bone intra-operatively commonly used with imageless computer-assist devices.

As used herein, the term "registration" refers to the determination of the spatial relationship between two or more objects or coordinate systems such as a computer-assisted surgical device, a bone, pre-operative bone data, surgical planning data (e.g., an implant model, cut-file, virtual boundaries, virtual planes, cutting parameters associated with or defined relative to the pre-operative bone data), and any external landmarks (e.g., a tracking marker array) associated with the bone or a tracked tool, if such landmarks exist. Illustrative methods of registration known in the art are described in U.S. Pat. Nos. 6,033,415, 8,010, 177, 8,036,441, and 8,287,522, and U.S. Pat. App. Pub. No. 2016/0338776.

As used herein, the term "real-time" refers to the processing of input data within milliseconds such that calculated values are available within 10 seconds of computational initiation.

Also described herein are 'computer-assisted surgical systems'. A computer assisted surgical system refers to any system (or device) requiring a computer to aid in a surgical procedure. Examples of a computer-assisted surgical device include a tracking system, tracked passive instruments, active or semi-active hand-held surgical devices and systems, autonomous serial-chain manipulator systems, haptic serial chain manipulator systems, parallel robotic systems, or master-slave robotic systems, as described in U.S. Pat. Nos. 5,086,401, 7,206,626, 8,876,830, 8,961,536, and 9,707,043, and WIPO App. No. PCT/US2015/051713.

Figure 2:
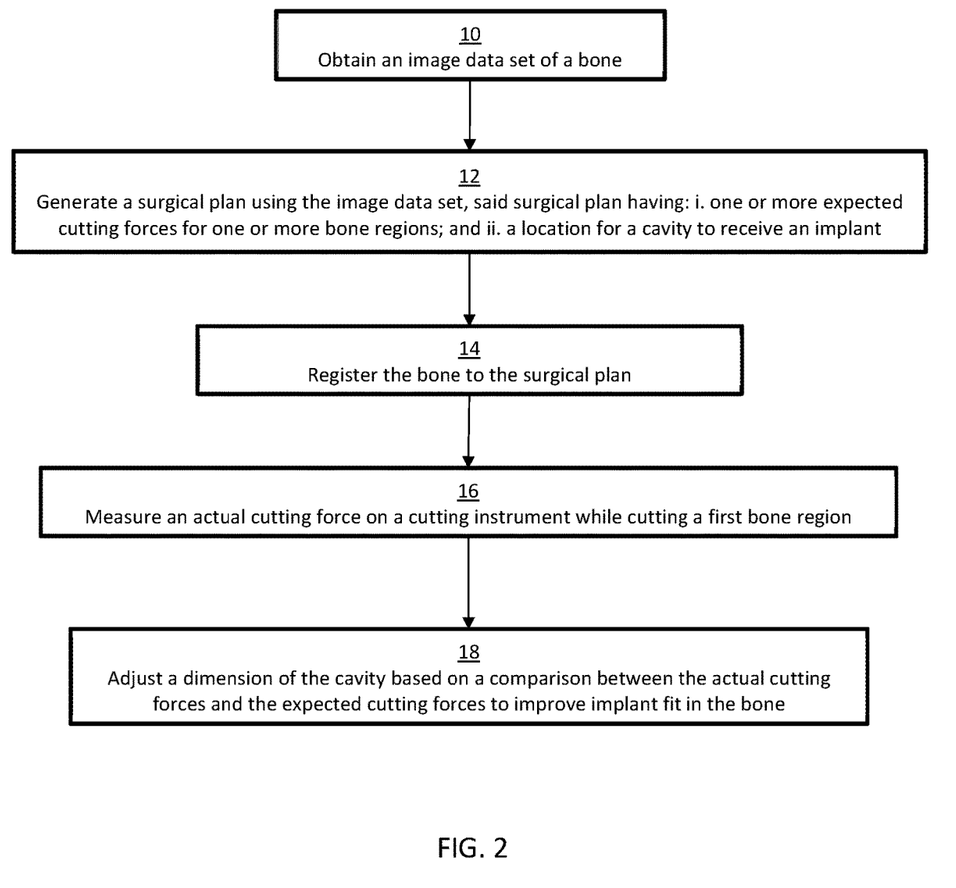
FIG. 2 is a flowchart of a method to intraoperatively adjust the dimensions of a pre-operatively planned implant cavity to improve implant fit in a bone in accordance with an embodiment of the invention.

With reference now to the drawings, FIG. 2 depicts an embodiment of a method to intraoperatively adjust the dimensions of a pre-operatively planned implant cavity to improve implant fit in a bone. An image data set of the bone is obtained preoperatively (Block 10). A surgical plan is generated using the image data set and/or a three-dimensional (3-D) bone model of the patient's bone generated from the image data set. The surgical plan includes: i. one or more expected cutting forces for one or more bone regions; and ii. a location for a cavity to receive an implant in a desired POSE (Block 12). Intraoperatively, the patient's bone is exposed and registered to the surgical plan and a computer assisted surgical system (Block 14). The computer assisted surgical system having a cutting tip and a force sensor for sensing forces exerted on the cutting tip creates an initial cut on the bone at a first bone region. The force sensor measures the actual cutting forces exerted on the cutting tip while cutting this first bone region (Block 16). Based on the difference between the actual cutting force and the expected cutting force in the plan, the dimensions of the cavity are adjusted accordingly (Block 18). For example, if the actual cutting forces are less than the expected cutting forces, which may indicate poorer bone quality than expected, then the dimensions of the cavity may be decreased to increase the press-fit and improve implant fit. Detailed embodiments of the method are further described below.

Figure 3:
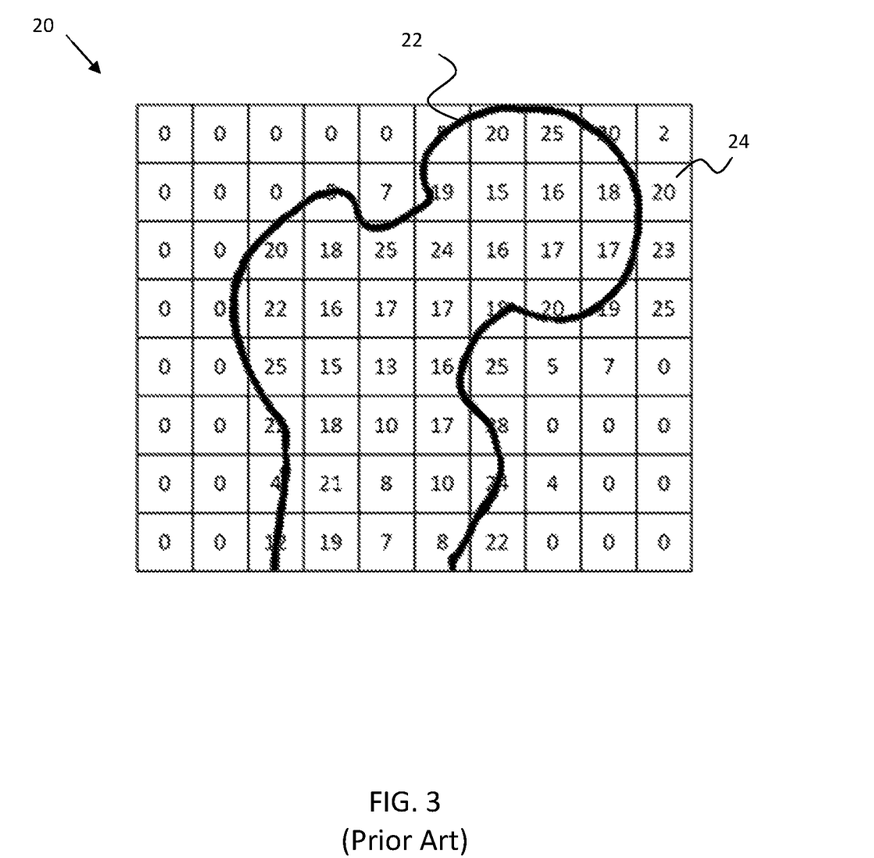
FIG. 3 is a prior art view of an image slice of an imaged bone with a plurality of values in and around the imaged bone that indicate the quality of the bone for different regions of the bone.

The image data set of a patient's bone may be obtained using an imaging modality such as computed tomography (CT), magnetic resonance imaging (MRI), ultrasound, dual-energy X-ray absorptiometry (DEXA), X-Ray, or fluoroscopy. The image data set may also be obtained by probing the exposed bone with a tracked device to generate a 3-D point cloud of the bone typical of many imageless computer surgical systems (e.g., NavioPFS® manufactured by Smith & Nephew). The image data set includes bone quality data associated with a plurality of bone regions. For example, with reference to FIG. 3, an image slice 20 of a CT scan of the patient's bone is illustratively depicted. The image slice 20 includes an imaged bone 22 and a plurality of values 24 in and around the imaged bone 22. The values 24 may indicate the quality of the bone for different regions of the bone. Bone quality may be measured as a function of bone density, architecture, composition, or a combination thereof. The bone quality may also be a relative value with respect to the bone itself, or absolute values relative to a known or standard scale. Further, it should be appreciated that the scale of FIG. 3 is exaggerated for the purpose of illustration and the values 24 may include or be substituted with other indicia including a color scale, color map, gray scale, pixel intensity, or a combination thereof. In a particular embodiment, the bone quality data is provided as Hounsfield units. In a specific embodiment, the bone quality data is provided as T-Scores and/or Z-scores from DEXA imaging.

The image data set may be used to aid a user in generating a surgical plan. The planning may occur in a planning software program. A 3-D model of the patient's bone may be generated from the image data set using methods known in the art. Pre-loaded implant models (e.g., CAD models of the implants) may be readily available to the user. The program includes widgets and other tools that allow the user to position the implant models relative to the 3-D bone model(s). The widgets and other tools may further allow the user to custom design implants on/around the 3-D model(s). In other embodiments, the user may plan the position for the implant directly on the image data set and may use the bone quality data to aid in planning the implant position. The planned POSE for the implant model relative to the data set and/or 3-D bone model engenders the POSE of the cavity to be created to receive the implant in the planned POSE as described above with reference to FIG. 1.

In particular inventive embodiments, the bone quality data is further correlated to cutting force data to generate the one or more expected cutting forces at one or more bone regions. For example, a higher Hounsfield unit at one bone region will correlate to a higher expected cutting force relative to lower Hounsfield unit bone regions. The correlation between bone quality data and cutting forces may be generated with several techniques as further described below. The final surgical plan therefore includes the location for a cavity to receive an implant and one or more expected cutting forces at one or more bone regions. This surgical plan is saved and/or transferred to a computer-assisted surgical device to execute the surgical plan.

Figure 4A:
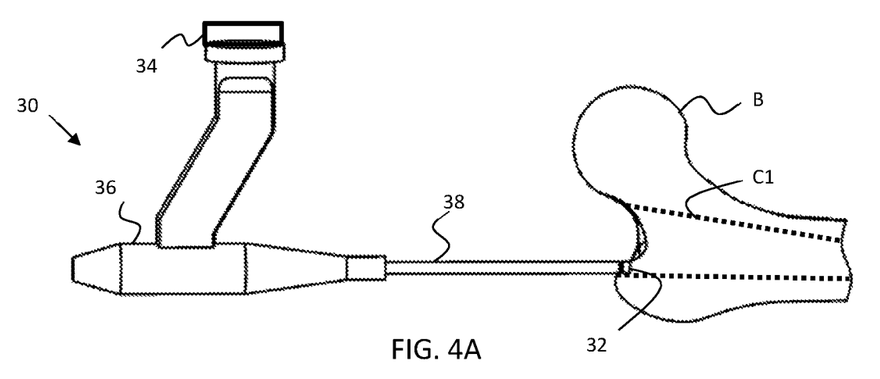
FIGS. 4A-4C, illustrate adjustments to cavity dimensions based on feedback of bone quality with a surgical device as a surgical robot having an end-effector assembly operating a cutting instrument with a 6-degree-of-freedom force sensor for sensing the forces exerted on the tip of the cutting instrument in accordance with embodiments of the invention.
Figure 4B:
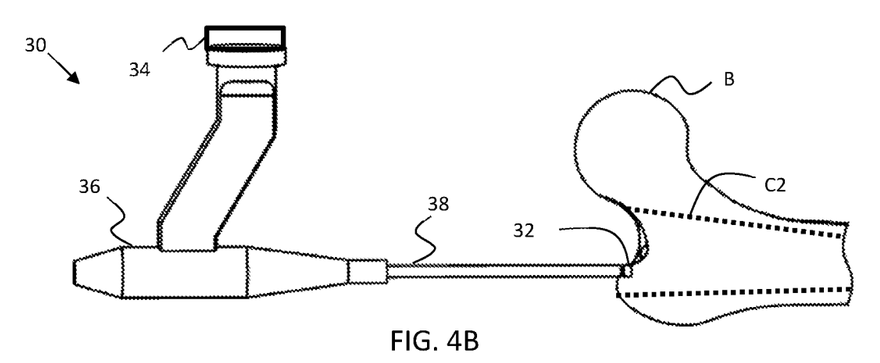
Figure 4C:
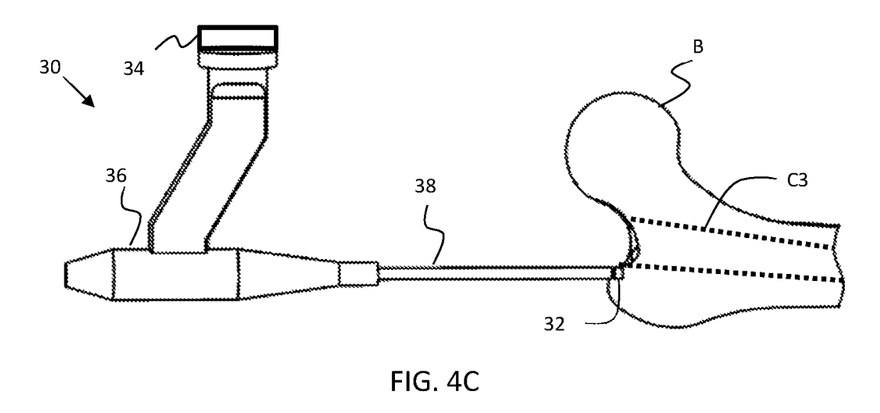

Intraoperatively, the patient's bone is exposed in a conventional fashion and registered to the surgical plan and the computer-assisted surgical device using techniques known in the art. With the bone registered, the surgical device knows of the POSE of the cavity to be created relative to the bone. In specific embodiments, with reference to FIGS. 4A to 4C, the surgical device is a surgical robot having an end-effector assembly 30 operating a cutting instrument 32 and a 3 to 6-degree-of-freedom force sensor or thermometer 34 for sensing the forces exerted on the cutting instrument 32. It is appreciated that other tool bits may be employed according to the present invention and that the end effector is only exemplary of these. The end-effector assembly 30 may include housing 36 enclosing a motor for rotating the cutting instrument 32. The cutting instrument 32 may include a shaft having a proximal end and a distal end, where the proximal end attaches with the motor and a the distal end includes teeth, flutes, edges, or other cutting structures for cutting, milling, grinding, or otherwise removing bone. Extending from the housing 36 is a sleeve 38 that surrounds and supports the shaft of the cutting instrument 32. The end-effector assembly 30 is attached to a distal link of the surgical robot. The surgical robot executes a cut-file, which is a set of instructions with the cutting parameters (e.g., cut paths, velocities, accelerations) to create the planned cavity C1. Prior to cutting the bone B, the surgical robot aligns the distal end or tip of the cutting instrument 32 with the first cut to be created as instructed by the cut-file. The cutting instrument 32 is turned-on and allowed to reach an operating spindle speed prior to cutting the bone B. Once the spindle speed is reached, the cutting instrument 32 creates an initial cut on the bone B (the initial cut is shown in FIGS. 4A to 4C). During cutting, the actual cutting forces are measured with the force sensor 34. The actual cutting forces are compared to the expected cutting forces defined in the surgical plan. Based on the comparison, the surgical device may pause the procedure and present the user with options to adjust the dimensions of the cavity. For example, the surgical device may pause and an alert or notification may appear on a display. It is appreciated that temperature is readily used as an indirect measure of force as under like tool operating conditions, normal bone cutting generates greater frictional forces and therefore heat that is manifest as a greater temperature increase as compared to osteoporotic bone. As such a thermometer such as a thermocouple in operative in the present invention in place of, or in conjunction with a force sensor.

With reference to FIG. 4B, the notification may inform the user that the actual forces are greater than the expected forces, in which event the user may have the option to increase the dimensions of the cavity, which will result in a larger cavity C2 than the planned cavity C1. In a specific inventive embodiment, the user may have the ability to manually adjust the dimensions of the cavity in one or more bone regions by providing input on the display. The display may include a model of the cavity superimposed on a model of the bone and/or implant where the user can adjust the dimensions of the cavity at one or more bone regions (e.g., by adjusting control points of splines or other parametric surfaces representing the cavity model or by adjusting a volumetric value of the cavity). The surgical device may provide instructions/recommendations for adjusting the dimensions of the cavity and in what regions of the bone. The surgical device may further limit the amount the user can manually adjust the cavity dimensions for safety. In another specific inventive embodiment, the device may automatically adjust the cavity by a set amount at one or more regions if the surgeon so chooses to make an adjustment.

In other specific inventive embodiments, with reference to FIG. 4C, the notification may inform the user that the actual forces are less than the expected forces, in which event the user may choose to decrease the dimensions of the cavity (increase press-fit), which will result in a smaller cavity C3 than the planned cavity C1. As above, the user may make manual adjustments to the cavity, or the device may automatically adjust the cavity dimensions after the user acknowledges and agrees to do so. It should be appreciated, that the actual cutting forces may be compared to the expected cutting forces for several bone regions prior to notifying, instructing, or automatically determining cavity adjustments. It is further contemplated, that the comparisons may happen in real-time for several bone regions while cutting the cavity, where the device may pause to notify, instruct, or automatically determine cavity adjustments only when encountering a threshold difference between the actual and expected forces. Once the cavity dimensions are adjusted in the surgical plan and/or processor/computer of the surgical device, the surgical device creates the cavity according to the adjusted dimensions. The implant is then placed in the cavity, the surgical site is closed, and the procedure is complete.

In specific inventive embodiments, the correlation between the bone quality data and the cutting forces is based on empirical studies. In one specific embodiment, a study of several cadaver cases may be performed. Image scans of the cadavers may be collected and the bone quality data from the image scans is measured for each bone region. The cadaver bones are then milled or cut with a surgical device while the cutting forces or temperature are measured for each bone region. The cutting forces are then correlated with the bone quality data in the image scans, bone region to bone region. In some embodiments, the cutting tip of the surgical device is tracked (e.g., by a mechanical robot arm, an optical tracking system), to ensure the measured forces at a particular bone region aligns with the bone quality data at that same region. In another embodiment, a correlation between the actual bone density and bone quality data is generated. The bone density of the cadaver bones is directly measured and correlated back to the bone quality data. Cutting forces may then be correlated directly to actual bone densities by cutting bone with a known bone density or phantoms having known bone densities. This method also results in a correlation between cutting forces and bone quality data.

The correlation between the bone quality data and the cutting forces may be based on historical data. For each patient case, the bone quality data and the forces measured during the procedure for the corresponding bone regions is stored. As the number of patient cases increases, the data increases and the correlation model improves. This model is routinely updated for each new patient case added to the model and used for all new patient cases.

In specific inventive embodiments, the surgical device may provide cavity adjustments recommendations and/or automatically determine the cavity adjustment based on empirical studies. A micro-motion study using cadaveric specimens may be performed to determine the relationship of the amount of pressfit required for a given set of bone densities. Image scans of the cadaveric specimens may further be collected and bone quality data extracted therefrom. The bone density of the cadavers may further be physically measured using techniques known in the art. In other embodiments, phantom models of bone may be created of mock bone material having known densities. The cadaver specimens, and/or phantom models, may be cut with varying cavity dimensions, wherein an implant is inserted therein and subjected to in-vivo like forces until failure. Therefore, the cavity dimensions, bone quality data, and potential clinical outcomes (e.g., subsidence, revision, and micro-motion) may be correlated. Based on the correlation, the device may recommend and/or automatically determine the cavity adjustments for the present patient case.

In particular inventive embodiments, the surgical device may provide cavity adjustment recommendations and/or automatically determine the cavity adjustment based on historical data and machine learning. For each patient case, the size of the cavity, bone quality data, and clinical outcomes are stored. The data continually increases to build a model correlating cavity size, bone quality data, and clinical outcomes. Based on the model, the surgical device has the ability to provide a course of action to adjust the size of the cavity. For example, the surgical device may create an initial cut and provide a notification to the user that by reducing the size of the cavity in a particular bone region or overall, then the probability of the implant subsiding decreases. The surgeon may then have the option to implement this recommendation.

In specific inventive embodiments, acoustic data may be used in lieu or in addition to the force sensor data or temperature data as described in co-pending provisional application 62/680,407 incorporated by reference herein in its entirety. Likewise, electrical current data is used as there is a different amount of electrical current required to cut harder bone compared to softer bone is therefore also an indirect measure of cutting force. It should be appreciated that the aforementioned empirical studies and historical data may utilize acoustic data or electrical current data in lieu of or in addition to the force sensor data or temperature data.

Surgical System

Figure 5:
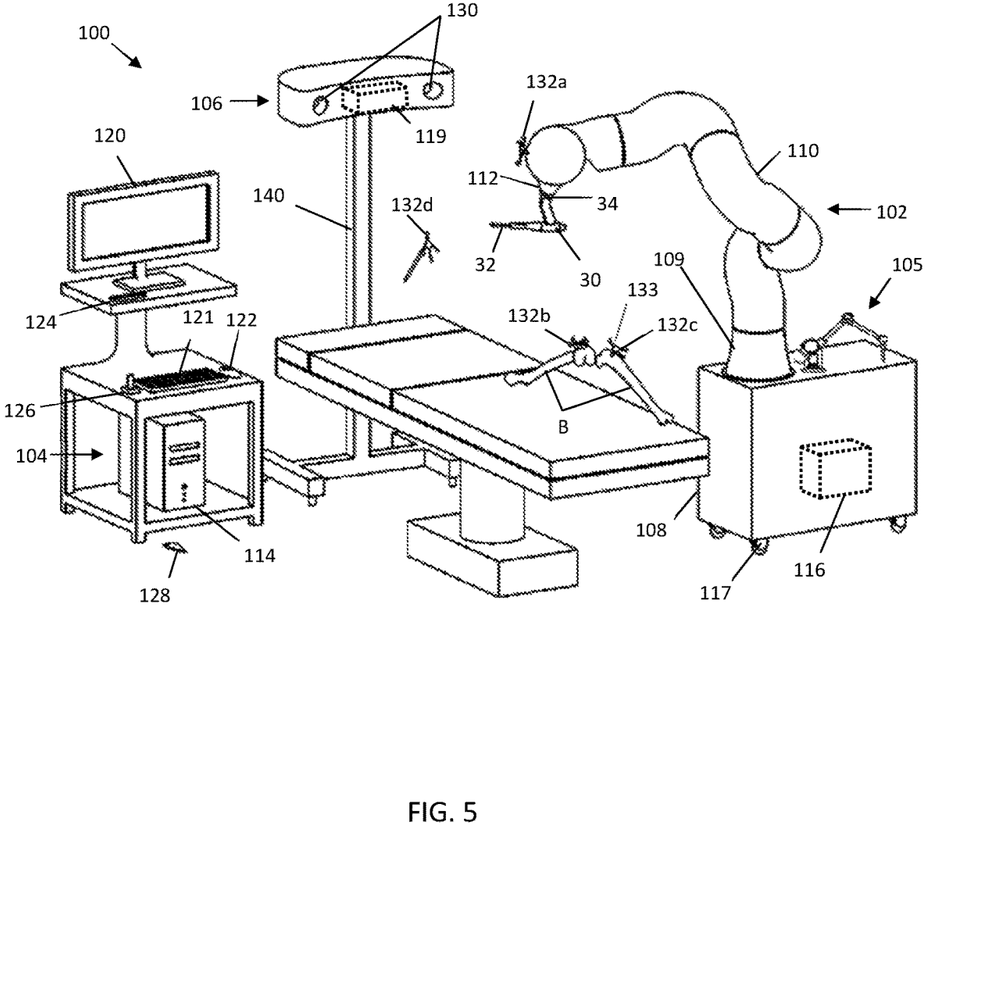
FIG. 5 shows an example of a computer-assisted surgical device in the context of an operating room (OR) for implanting embodiments of the invention.

With reference to FIG. 5, an example of a computer-assisted surgical system 100 for computer-assisted surgery device 102 in the context of an operating room (OR) is shown. The surgical system 100 generally includes a surgical robot 102, a computing system 104, a mechanical arm 105 and/or a non-mechanical tracking system 106 (e.g., an optical tracking system, an electro-magnetic tracking system).

The surgical robot 102 may include a movable base 108, a manipulator arm 110 connected to the base 108, an end-effector flange 112 located at a distal end of the manipulator arm 110, and an end-effector assembly 30 removably attached to the flange 112. The end-effector assembly 30 holds and/or operates a cutting instrument 32 that interacts with a portion of a patient's anatomy. Proximal to the flange 112 is a force sensor or thermometer 34 for sensing forces experienced on the cutting instrument. The base 108 includes a set of wheels 117 to maneuver the base 108, which may be fixed into position using a braking mechanism such as a hydraulic brake. The base 108 may further include an actuator 109 to adjust the height of the manipulator arm 110. The manipulator arm 110 includes various joints and links to manipulate the tool 32 in various degrees of freedom. The joints are illustratively prismatic, revolute, spherical, or a combination thereof. The surgical robot 102 may further include a tracking array 132a to track the position of the cutting instrument 32. The tracking array 132a may be attached to the end-effector assembly 30 or cutting instrument 32 directly, or the tracking array 132a may be positioned on the base 108 or a link of the surgical robot 102 where the kinematics of the surgical robot is used with the tracking data to track the POSE of the cutting instrument 32.

The computing system 104 generally includes a planning computer 114; a device computer 116; an optional tracking computer 119 if a tracking system 106 is present; and peripheral devices. The planning computer 114, device computer 116, and tracking computer 119, may be separate entities, one-in-the-same, or combinations thereof depending on the surgical system. Further, in some embodiments, a combination of the planning computer 114, the device computer 116, and/or tracking computer 119 are connected via a wired or wireless connection. The peripheral devices allow a user to interface with the robotic surgical system 100 and may include: one or more user-interfaces, such as a display or monitor 120; and user-input mechanisms, such as a keyboard 121, mouse 122, pendent 124, joystick 126, foot pedal 128, or the monitor 120 in some inventive embodiments may have touchscreen capabilities.

The planning computer 114 contains hardware (e.g., processors, controllers, and memory), software, data and/or utilities that are in some inventive embodiments dedicated to the planning of a surgical procedure, either pre-operatively or intra-operatively. This may include reading medical imaging data, segmenting imaging data, constructing three-dimensional (3D) virtual models, storing computer-aided design (CAD) files, highlighting and/or identifying bone regions for bone quality analysis, modeling the bones range-of-motion, executing finite element analysis, and generating final surgical plan data. The planning computer 114 may further provide functions to define or correlate expected cutting forces or bone quality data to pre-operative bone data utilizing any of the aforementioned methods. The final surgical plan may include image data of the bones, patient data, expected cutting force data, registration data, implant position data, the location of bone regions for bone quality analysis, operational data for modifying a volume of tissue that is defined relative to the anatomy, such as a cutting parameters (e.g., cut paths, velocities) defined in a cut-file to autonomously modify the volume of bone, a set of virtual boundaries defined to haptically constrain a tool within the defined boundaries to modify the bone, a set of planes or drill holes to drill pins in the bone, or a graphically navigated set of instructions for modifying the tissue, and combinations thereof. In specific inventive embodiments, the operational data is a cut-file for a surgical robot to autonomously modify the volume of bone, which is advantageous from an accuracy and usability perspective. The data generated from the planning computer 114 may be transferred to the device computer 116 and/or tracking computer 119 through a wired or wireless connection in the operating room (OR); or transferred via a non-transient data storage medium (e.g., a compact disc (CD), a portable universal serial bus (USB) drive).

The device computer 116 in some inventive embodiments is housed in the moveable base 108 and contains hardware (e.g., controllers), software, data and utilities that are preferably dedicated to the operation of the surgical robot 102. This may include surgical device control, robotic manipulator control, the processing of kinematic and inverse kinematic data, the execution of registration algorithms, correlating the force data to the bone quality data or expected cutting force data in the plan, the execution of calibration routines, the execution of surgical plan data, coordinate transformation processing, providing workflow instructions to a user, comparing pre-operative data to intra-operatively collected data, providing the notifications and recommendations to adjust the cavity dimensions, automatically determining cavity dimension adjustments, utilizing position and orientation (POSE) data from the tracking system 106, and reading data received from the force sensor 34, temperature sensor, and/or mechanical arm 105.

The optional tracking system 106 of the surgical system 100 may be an optical tracking system as described in U.S. Pat. No. 6,061,644. The optical tracking system includes two or more optical receivers 130 to detect the position of tracking arrays (132a, 132b, 132c, 123d), where each tracking array (132a, 132b, 132c, 132d) has a unique arrangement of fiducial markers 133, or a unique transmitting wavelength/frequency if the markers 133 are active LEDs. The tracking system 106 may be built into a surgical light, located on a boom, a stand 140, or built into the walls or ceilings of the OR. The tracking system computer 136 may include tracking hardware, software, data and utilities to determine the POSE of objects (e.g., bones, and surgical robot 102) in a local or global coordinate frame. The POSE of the objects is collectively referred to herein as POSE data, where this POSE data may be communicated to the device computer 116 through a wired or wireless connection. Alternatively, the device computer 116 may determine the POSE data using the position of the fiducial markers detected from the optical receivers 130 directly.

The POSE data is used by the computing system 104 during the procedure to update the POSE and/or coordinate transforms of the bone B, the surgical plan, and the surgical robot 102 as the manipulator arm 110 and/or bone B move during the procedure, such that the surgical robot 102 can accurately execute the surgical plan. In another embodiment, the surgical system 100 does not include a tracking system 106, but instead employs a mechanical arm 105, and a bone fixation and monitoring system that fixes the bone directly to the surgical robot 102 and monitors bone movement as described in U.S. Pat. No. 5,086,401.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A method to intraoperatively adjust the dimensions of a pre-operatively planned implant cavity to improve implant fit, the method comprising:
   obtaining an image data set of a bone;
   generating a surgical plan using the image data set, the surgical plan comprising: (i) one or more expected cutting forces or cutting temperatures for one or more bone regions; and (ii) a location for the pre-operatively planned implant cavity to receive an implant in a predetermined position and orientation (POSE);
   registering the surgical plan to the bone in a coordinate system of a computer assisted surgical system;
   measuring an actual cutting force or cutting temperature on a cutting instrument while cutting a first bone region;
   comparing the actual cutting force or cutting temperature to the one or more expected cutting forces or cutting temperatures; and
   adjusting a dimension of the cavity based on the comparing to improve implant fit.

2. The method of claim 1 wherein the computer assisted surgical system further comprises a force sensor that measures the actual cutting force on the cutting instrument.

3. The method of claim 1 wherein if the actual cutting force is less than the one or more expected cutting forces, the dimension of the cavity is decreased.

4. The method of claim 1 wherein if the actual cutting force is more than the one or more expected cutting forces, the dimension of the cavity is increased.

5. The method of claim 1 wherein the computer assisted surgical system further comprises a thermocouple that measures the actual temperature on the cutting instrument.

6. The method of claim 1 wherein the image data set of the bone is obtained using an imaging modality comprising one of: computed tomography (CT), magnetic resonance imaging (MRI), ultrasound, dual-energy X-ray absorptiometry (DEXA), X-Ray, or fluoroscopy.

7. The method of claim 1 wherein the image data set of the bone is obtained by probing an exposed portion of the bone with a tracked device to generate a 3-D point cloud of the bone.

8. The method of claim 1 wherein the image data set of the bone comprises bone quality data associated with the one or more bone regions.

9. The method of claim 8 wherein the bone quality data is measured as a function of bone density, architecture, composition, or a combination thereof.

10. The method of claim 8 wherein the bone quality data is a relative value with respect to the bone itself, or absolute values relative to a known or standard scale.

11. The method of claim 8 wherein the bone quality data is provided as Hounsfield units.

12. The method of claim 8 wherein the bone quality data is provided as T-Scores or Z-scores from dual-energy X-ray absorptiometry imaging.

13. The method of claim 8 wherein the bone quality data is further correlated to cutting force data to generate the one or more expected cutting forces at the one or more bone regions.

14. The method of claim 1 wherein the surgical plan is generated by a planning software program.

15. The method of claim 14 wherein the planning software generates a three-dimensional (3D) model of the bone; and wherein the planning software further comprises widgets and other tools to allow a user to position pre-loaded implant models relative to the 3-D bone model to determine a POSE of the pre-operatively planned implant cavity.

16. The method of claim 1 wherein the computer assisted surgical system generates a notification to inform a user that the actual cutting force differs from the one or more expected cutting forces.

17. The method of claim 16 wherein the actual cutting forces are compared to the expected cutting forces for several bone regions prior to notifying, instructing, or automatically determining cavity adjustments.

18. The method of claim 16 wherein the comparing occurs in real-time for several bone regions while cutting the cavity, where the cutting instrument is paused to notify, instruct, or automatically determine cavity adjustments only when encountering a threshold difference between the actual and expected cutting forces.

19. The method of claim 16 wherein the computer assisted surgical system provides cavity adjustment recommendations or automatically determines the cavity adjustment based on historical data and machine learning; and storing for each patient case, the size of the cavity, bone quality data, and clinical outcomes to build a model correlating cavity size, bone quality data, and clinical outcomes to determine cavity adjustments for a present patient case.

* * * * *